United States Patent
McCoy (10) Patent No.: US 9,745,571 B2
(45) Date of Patent: Aug. 29, 2017

(54) REPETITIVE REVERSE TRANSCRIPTION PARTITION ASSAY

(71) Applicant: Bio-Rad Laboratories, Inc., Hercules, CA (US)

(72) Inventor: Adam M. McCoy, Davis, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 661 days.

(21) Appl. No.: 14/201,103

(22) Filed: Mar. 7, 2014

(65) Prior Publication Data

US 2014/0256585 A1 Sep. 11, 2014

Related U.S. Application Data

(60) Provisional application No. 61/774,277, filed on Mar. 7, 2013.

(51) Int. Cl.
*C12Q 1/68* (2006.01)
*C12N 15/10* (2006.01)

(52) U.S. Cl.
CPC ....... *C12N 15/1075* (2013.01); *C12Q 1/6851* (2013.01)

(58) Field of Classification Search
None
See application file for complete search history.

(56) References Cited

U.S. PATENT DOCUMENTS

| | | | |
|---|---|---|---|
| 6,271,002 B1 | 8/2001 | Linsley et al. | |
| 6,946,251 B2 * | 9/2005 | Kurn | C12Q 1/6853 435/6.1 |
| 2005/0003380 A1 * | 1/2005 | Cohen | C12N 15/1058 435/6.11 |
| 2007/0077570 A1 * | 4/2007 | Lao | C12Q 1/6851 435/6.12 |
| 2007/0134652 A1 * | 6/2007 | Slepnev | C12Q 1/6851 435/5 |
| 2010/0173394 A1 | 7/2010 | Colston et al. | |
| 2010/0203538 A1 | 8/2010 | Dube et al. | |
| 2010/0221786 A1 * | 9/2010 | Jeong | C12Q 1/6846 435/91.2 |
| 2011/0065606 A1 * | 3/2011 | Janulaitis | C12N 9/1276 506/11 |
| 2011/0159551 A1 | 6/2011 | Xi et al. | |
| 2011/0212846 A1 * | 9/2011 | Spier | C12Q 1/686 506/7 |
| 2012/0316074 A1 | 12/2012 | Saxonov et al. | |
| 2013/0217071 A1 * | 8/2013 | Montesclaros | C12P 19/34 435/91.2 |
| 2014/0349858 A1 * | 11/2014 | Motley | C12Q 1/70 506/2 |

FOREIGN PATENT DOCUMENTS

| | | | | |
|---|---|---|---|---|
| WO | WO 2010036352 A1 * | 4/2010 | | B01F 3/0807 |
| WO | WO 2011020011 A2 * | 2/2011 | | B01L 3/502792 |
| WO | WO 2013130512 A2 * | 9/2013 | | C12Q 1/6853 |

OTHER PUBLICATIONS

Kirshenboim et al., Expression and characterization of a novel reverse transcriptase of the LTR retrotransposon Tf1, Virology. Sep. 30, 2007;366(2):263-76. Epub May 23, 2007.*
Malboeuf et al., Thermal effects on reverse transcription: improvement of accuracy and processivity in cDNA synthesis, Biotechniques. May 2001;30(5):1074-8, 1080, 1082, passim.*
Smith (Absolute Quantification with Digital PCR, Biocompare, editorial, attached, Feb. 22, 2012).*
BioRad (Absolute Quantification with Digital PCR, attached, May 14, 2012).*
Zhang et al. (Massively parallel single-molecule and single-cell emulsion reverse transcription polymerase chain reaction using agarose droplet microfluidics, Anal Chem. Apr. 17, 2012;84(8):3599-606. Epub Apr. 4, 2012).*
Beer et al. (On-chip single-copy real-time reverse-transcription PCR in isolated picoliter droplets, Anal Chem. Mar. 15, 2008;80(6):1854-8. Epub Feb. 16, 2008).*
Applied Biosystems (GeneAmp® AccuRT RNA PCR Kit and GeneAmp® AccuRT Hot Start RNA PCR Kit, attached, Aug. 21, 2004).*
BioRad (hereinafter "BioRad2"; Droplet Digital PCR, attached, Jan. 2, 2010).*
International Search Report and Written Opinion dated May 28, 2014 for International Patent Application No. PCT/US2014/022103.

* cited by examiner

*Primary Examiner* — Aaron Priest
(74) *Attorney, Agent, or Firm* — Kilpatrick Townsend & Stockton LLP (57) ABSTRACT

Methods, compositions, and kits are provided for quantifying RNA molecules in a partitioned sample via multiple reverse transcription reactions.

18 Claims, 2 Drawing Sheets

REPETITIVE REVERSE TRANSCRIPTION PARTITION ASSAY

CROSS-REFERENCE TO RELATED APPLICATION

This application claims priority to U.S. Provisional Patent Application No. 61/774,277 filed Mar. 7, 2013, the contents of which are hereby incorporated in the entirety for all purposes.

BACKGROUND OF THE INVENTION

Amplification of nucleic acid molecules is routinely practiced in medical and bioresearch settings for a variety of tasks, such as the detection of hereditary diseases, the identification of genetic fingerprints, the diagnosis of infectious diseases, the cloning of genes, paternity testing, and other types of nucleic acid analysis. Nucleic acid amplification techniques include, but are not limited to, PCR, the ligase chain reaction (LCR), the transcription based amplification system (TAS), the nucleic acid sequence-based amplification (NASBA), the strand displacement amplification (SDA), rolling circle amplification (RCA), and hyperbranched RCA (HRCA).

Digital amplification is a technique that allows quantitative measurement of the number of target molecules in a sample. The basic premise of the technique is to divide a large sample into a number of smaller subvolumes (partitioned volumes), whereby the subvolumes contain on average a low number or single copy of target. Then, by counting the number of successful amplification reactions in the subvolumes, one can deduce the starting copy number of the target in the sample.

In some cases, target nucleic acids can be difficult to amplify. Amplification reactions that fail for reasons unrelated to the presence or absence of target nucleic acid in a bulk solution will distort statistical analysis of the results, and result in an incorrect determination of the quantity of target molecules present in a sample. For example, RNA molecules which are typically subject to a reverse transcription reaction prior to amplification can confound quantitative analysis by amplification due to bias introduced during the reverse transcription step. Sources of bias introduced by reverse transcription can include poor processivity and fidelity of the reverse transcriptase, RNA secondary structure, and degradation or poor quality of target RNA molecules. RNAs that are readily transcribed into DNA can be artificially increased in apparent abundance, while RNAs that are difficult to transcribe into DNA can be artificially reduced in apparent abundance. Generally multiple rounds of reverse transcription exacerbate bias because RNA molecules that fail to be transcribed into DNA during one round are likely to fail during subsequent rounds of reverse transcription. Additionally, RNA molecules that are transcribed readily during one round, are likely to be transcribed readily during subsequent rounds. Thus, multiple rounds of reverse transcription in a bulk solution can further artificially increase the apparent abundance of readily transcribed RNAs and artificially decrease the apparent abundance of RNAs that are difficult to transcribe.

BRIEF SUMMARY OF THE INVENTION

In one embodiment, the invention provides a method of quantifying one or more target RNA(s) in a biological sample, the method comprising, incubating a plurality of mixture partitions of the sample, wherein the mixture comprises the sample and a reverse transcriptase, under conditions such that at least two rounds of reverse transcription occurs in the partitions, thereby generating one or more cDNA(s) complementary to at least 10 contiguous nucleotides of the target RNA in partitions having the target RNA; quantifying the number of partitions containing the cDNA(s); and correlating the number of partitions containing the cDNA(s) to the quantity of the one or more target RNA(s) in the sample, thereby quantifying the one or more target RNA(s) in the sample.

In one aspect, the incubating comprises incubating at least 100 mixture partitions.

In another aspect, the method comprises contacting the reverse transcriptase to the sample to form the mixture; and partitioning the mixture to generate the plurality of partitions.

In some cases, the step of contacting the reverse transcriptase to the sample is performed at a temperature of less than about 25° C.

In some cases, the reverse transcriptase comprises a hot start reverse transcriptase.

In another aspect, the method comprises partitioning the sample to generate the plurality of partitions; and contacting the partitions with the reverse transcriptase, thereby generating the plurality of mixture partitions.

In yet another aspect, the incubating step comprises generating cDNA(s) comprising molecular barcodes such that cDNA(s) from different partitions can be distinguished; the method further comprising, disrupting and combining the partitions to form a solution comprising barcoded cDNA(s); and quantifying the number of partitions containing cDNA(s) by detecting the barcodes and counting a number of unique detected barcodes, wherein the number of unique detected barcodes is correlated with the number of mixture partitions containing the target RNA.

In some cases, the cDNA(s) comprise double-stranded cDNA(s) and both strands contain a barcode. The barcode can be the same for each strand or different for each strand.

In some cases, the method further comprises quantifying multiple target RNAs by counting the number of unique detected barcodes of each of the cDNA(s) complementary to each target RNA, wherein the number of unique detected barcodes of each of the cDNA(s) complementary to each target RNA is correlated with the number of mixture partitions containing each target RNA.

In another aspect of the invention, the conditions of at least one of the rounds of reverse transcription comprises denaturation conditions such that secondary structure(s) in the target RNA, if present, are reduced.

In some cases, the denaturation conditions comprise heat, chemicals, helicases, or strand displacing enzymes.

In some cases, the reverse transcriptase comprises strand displacement activity. In some aspects, the reverse transcriptase is Tth polymerase, and the partition mixtures comprise manganese ions.

In some cases, the reverse transcriptase is heat tolerant, and the denaturation conditions comprise elevating the temperature of the mixture to at least 50, 55, 60, 65, 70, 75, 80, 85, 90, 95, or 99° C. or higher.

In some cases, the partition mixtures comprise a strand-displacing reverse transcriptase, and multiple rounds of reverse transcription are performed in the partition mixtures by incubating the partition mixtures at a temperature of about 15, 20, 25, or 30° C. for at least about 45, 60, 70, 80, 90, 100, 120 minutes or longer.

In some cases, the partition mixtures are not heated to a temperature above about 60, 65, 70, 75, 80, 85, 90, 95° C. or higher between the multiple rounds of reverse transcription.

In one aspect of the invention, a round of reverse transcription is terminated by a denaturation event. Alternatively, at least two rounds of reverse transcription are each terminated by a denaturation event. In such cases, the reverse transcriptase can be Tth polymerase, and the partition mixtures comprise manganese ions.

In some cases, the denaturation event comprises heating the partition mixtures to a temperature of at least 50, 55, 60, 65, 70, 75, 80, 85, 90, 95, or 99° C. or higher, contacting the partition mixtures with a chemical denaturant, or contacting the partition mixtures with a helicase.

In some cases, the partition mixtures comprise a chemical denaturant at a concentration insufficient to substantially interfere with the step of reverse transcription, and the denaturation event comprises heating the partition mixtures to a temperature below 50, 55, 60, 65, 70, 75, 80, 85, or 90, ° C.

In some cases the partition mixtures can comprise a reversible light induced pH shifting dye, and wherein the denaturation event comprises inducing a reversible light induced pH shift.

In some cases, the partition mixtures further comprise a chemical denaturant at a concentration insufficient to substantially interfere with the step of reverse transcription.

In some cases, the partition mixtures comprise a reversible light induced pH shifting dye, and the denaturation event comprises inducing a reversible light induced pH shift and heating the partition mixtures to a temperature below 50, 55, 60, 65, 70, 75, 80, 85, or 90, ° C.

In some cases, the reverse transcriptase is Tth polymerase, and the partition mixtures comprise manganese ions.

In some cases, the partition mixtures comprise a reversibly inactivated reverse transcriptase and the denaturation event comprises lowering the temperature below about 25, 30, 35, 40, or 50° C.

The quantifying can comprise amplifying the cDNA(s). In some embodiments, the quantifying can comprise amplifying the cDNA(s) in the partitions.

The quantifying can additionally or alternatively comprise determining a relative level of two or more target RNAs from the same sample, or determining an absolute level of two or more target RNAs from the same sample.

In some cases, the partitions are droplets. The droplets can be surrounded by an immiscible carrier fluid. In other cases, the partitions are micro channels.

In some cases, the target RNA is a rare transcript or is present in the sample at a frequency of about 100 target RNA molecules per microliter or lower.

In some cases, the target RNA comprises significant secondary structure at a temperature of about 30, 35, 40, 45, 50, 55, 60, 65, 70, or 75° C. or higher.

In some cases, the target RNA comprises a low complexity region.

DEFINITIONS

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier ($4^{th}$ ed. 2007); Sambrook et al., MOLECULAR CLONING, A LABORATORY MANUAL, Cold Spring Harbor Lab Press (Cold Spring Harbor, N.Y. 1989). The term "a" or "an" is intended to mean "one or more." The term "comprise," and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

As used herein, the term "partitioning" or "partitioned" refers to separating a sample into a plurality of portions, or "partitions." Partitions can be solid or fluid. In some embodiments, a partition is a solid partition, e.g., a micro channel. In some embodiments, a partition is a fluid partition, e.g., a droplet. In some embodiments, a fluid partition (e.g., a droplet) is a mixture of immiscible fluids (e.g., water and oil), or an emulsion. In some embodiments, a fluid partition (e.g., a droplet) is an aqueous droplet that is surrounded by an immiscible carrier fluid (e.g., oil). In other embodiments, a fluid partition is an aqueous droplet that is physically or chemically separated from adjacent aqueous droplets such that template and product nucleic acid in one droplet do not diffuse into adjacent droplets.

The term "probe" refers to a molecule (e.g., a protein, nucleic acid, aptamer, etc.) that specifically interacts with or specifically binds to a target molecule. Non-limiting examples of molecules that specifically interact with or specifically bind to a target molecule include nucleic acids (e.g., oligonucleotides), proteins (e.g., antibodies, transcription factors, zinc finger proteins, non-antibody protein scaffolds, etc.), and aptamers.

A "target molecule" refers to a molecule to be detected in a sample. In some embodiments, the target molecule is a peptide, protein (e.g., an antibody, enzyme, growth regulator, clotting factor, or phosphoprotein), polynucleotide (e.g., DNA, such as dsDNA or ssDNA; RNA, such as mRNA or miRNA; or a DNA-RNA hybrid), aptamer, peptide nucleic acid, carbohydrate, virus, virus-like particle, drug compound, metabolite, or cell. In some embodiments, two or more target molecules to be detected in a sample comprise a complex of interacting target molecules (e.g., a ligand-receptor complex of proteins).

The term "binds," with respect to a probe binding to a target molecule, typically indicates that the probe (e.g., an oligonucleotide or an antibody) binds a majority of the target molecule in a pure population, assuming an appropriate molar ratio of probe to target molecule. For example, a probe that binds a given target molecule typically binds to at least ⅔ of the target molecules in a solution (e.g., 67%, 75%, 80%, 85%, 90%, 91%, 92%, 93%, 94%, 95%, 96%, 97%, 98%, 99%, or 100%). One of skill will recognize that some variability will arise depending on the method and/or threshold of determining binding.

The term "specifically binds to" or "specifically interacts with" refers to a probe (e.g., an oligonucleotide or an antibody) that binds to a target molecule with at least 2-fold greater affinity than non-target molecules, e.g., at least 4-fold, 5-fold, 6-fold, 7-fold, 8-fold, 9-fold, 10-fold, 20-fold, 25-fold, 50-fold, or 100-fold greater affinity. For example, a probe that specifically binds a particular target molecule will typically bind the target molecule with at least a 2-fold greater affinity than a non-target molecule.

The terms "label" and "detectable label" interchangeably refer to a composition detectable by spectroscopic, photochemical, biochemical, immunochemical, chemical, or other physical means. For example, useful labels include fluorescent dyes, luminescent agents, radioisotopes (e.g., $^{32}$P, $^{3}$H), electron-dense reagents, enzymes, biotin, digoxigenin, or haptens and proteins, nucleic acids, or other entities which can be made detectable, e.g., by incorporating a radiolabel into an oligonucleotide, peptide, or antibody specifically reactive with a target molecule. Any method known in the art for conjugating an antibody to the label can be employed, e.g., using methods described in Hermanson, *Bioconjugate Techniques* 1996, Academic Press, Inc., San Diego.

A molecule that is "linked" to a label (e.g., as for a labeled probe as described herein) is one that is bound, either covalently, through a linker or a chemical bond, or noncovalently, through ionic, van der Waals, electrostatic, or hydrogen bonds to a label such that the presence of the molecule can be detected by detecting the presence of the label bound to the molecule.

DETAILED DESCRIPTION OF THE INVENTION

I. Introduction

Methods, compositions, and kits are provided for quantifying one or more target RNA molecules in a sample using multiple rounds of reverse transcription. For example, methods, compositions, and kits are provided for quantifying one or more target RNA molecules in a sample by digital amplification. Such methods, compositions, and kits can be useful for determining the relative or absolute expression level of a target messenger RNA molecule in a sample. In some cases, the methods, compositions, and kits of the present invention can provide absolute or relative quantification of RNA templates that are difficult to reverse transcribe, or are present in low abundance. In some cases, the methods, compositions and kits of the present invention provide absolute or relative quantification of RNA templates with reduced bias.

Figure 1:
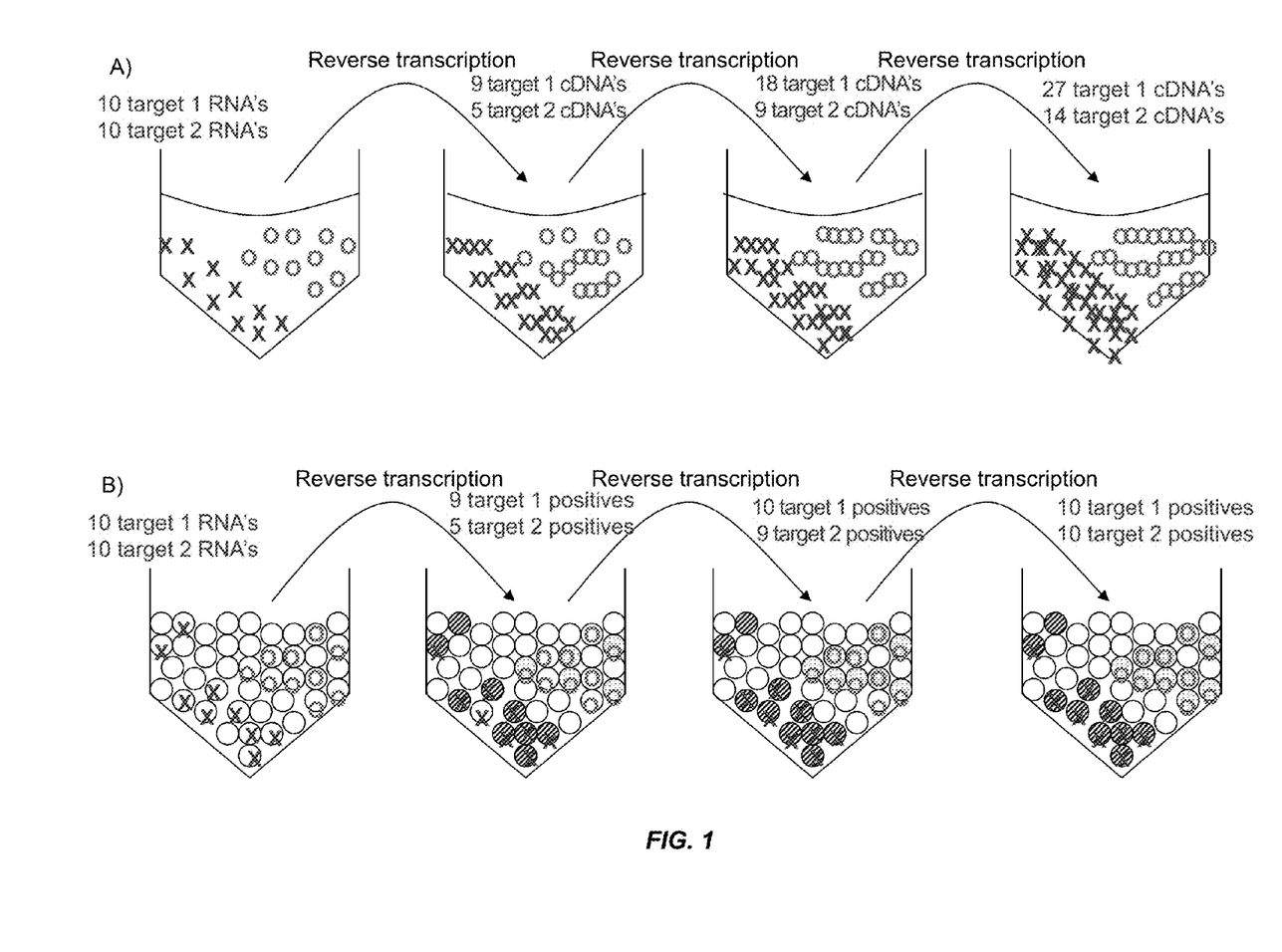
FIG. 1, illustration of the difference between repeated reverse transcriptase reactions in bulk solution (A) and in partitions (B). The example shows two targets with different reverse transcriptase efficiencies. Target 1 (illustrated as "X") has approximately 90% reverse transcriptase efficiency per round. Target 2 (illustrated as "O") has approximately 45% RT efficiency. Partitions in which the target RNA is successfully detected are depicted as circles filled with diagonal lines for target 1 and circles filled with vertical and horizontal lines for target 2. The results after 3 rounds of reverse transcription are shown.

Samples can be partitioned into a number of partitions, reverse transcribed, amplified, and analyzed for the presence or absence of the amplified target nucleic acid using digital analysis. The reverse transcription step can be performed more than once, e.g. 2, 3, 4, 5, 6, 7, 8, 10 or more times. The use of multiple rounds of reverse transcription for quantification of RNA is generally avoided in standard protocols due to the introduction and exacerbation of bias. The differential efficiency of the reverse transcription step can confound absolute measurements of RNA by providing inaccurate quantification of some targets. The differential efficiency of reverse transcription can also confound relative quantification. In standard protocols, multiple rounds of reverse transcription can increase or exacerbate these confounding effects. However, the methods, compositions and kits provided herein address this problem through the use of a partitioning step. In part, bias introduced by multiple rounds of reverse transcription is reduced or eliminated by partitioning because each partition is interrogated for a presence or absence of a target RNA rather than a quantity. The presence or absence of the target RNA in a number of partitions then provides absolute or relative quantification. In a suitably partitioned sample with digital quantification, additional rounds of reverse transcription can decrease the number of partitions with a target that fail to produce a detectable signal, but do not alter the signal from otherwise positive partitions or partitions that lack a target. Therefore, methods utilizing multiple rounds of reverse transcription and partitioning of a sample increase the sensitivity and accuracy of quantification of RNA without introducing many of the problems of bias that generally preclude one of skill in the art from using multiple rounds at the reverse transcription step. (FIG. 1) Thus, the methods described herein allow for improved sensitivity of detecting a target molecule or molecules and precise absolute or relative quantification of the target molecule or molecules, and lower the limits of direct detection of target molecules in a sample.

Partitioning can be performed before initiation of reverse transcription. For example, samples containing target RNA molecules can be partitioned in droplets or micro channels, and reverse transcription performed at least two times therein. In some cases, samples containing target RNA molecules can be subject to a reverse transcription reaction, partitioned and then subject to further rounds of reverse transcription.

II. Generation of cDNA

Double- or single stranded DNA molecules can be synthesized from target RNAs (or other single-stranded nucleic acids), e.g., mRNAs present in a population of cells, by a variety of methods. These methods can employ a polymerase that comprises an RNA-dependent DNA polymerase activity. In some embodiments, all, substantially all, or a majority of the RNA-dependent DNA polymerization is performed after partitioning of the sample. RNA-dependent DNA polymerase activity utilizes one or more primers for synthesis of a first strand of DNA complementary to the target RNA molecule. Additionally, synthesis of a second strand of DNA that is complementary to the first strand can also utilize a primer. Such primers can be prepared using any suitable method known in the art.

a. Multi-Round Reverse Transcription

Reverse transcription can be performed multiple times. For example, reverse transcription can be performed at least 2, 3, 4, 5, 6, 7, 8, 9, 10, 10-15, 15-20, 20-30, or more times. In some embodiments, reverse transcription is performed multiple times after partitioning of a sample into multiple partition mixtures. In some cases, a majority of the multiple partition mixtures each comprise a small number (e.g., about 2, 3, 4, 5, 6, 7, 8, 9, 10, or more copies), or a single copy, of target RNA. In some cases, first strand synthesis is initiated multiple times, and second strand synthesis performed one time. In other cases, first and second strand synthesis are both performed multiple times. In still other cases, first strand synthesis is performed multiple times, and second strand synthesis is not performed.

Partitioning of a sample and initiating multiple rounds of reverse transcription within the partitions can increase the sensitivity and accuracy of quantification of RNA by digital amplification methods without introducing many of the problems with bias that teach against the use of such multiple rounds. For example, multiple rounds of reverse transcription can increase the amount of DNA generated from RNA, allowing a lower limit of detection. Similarly, multiple rounds of reverse transcription might increase the probability of successful reverse transcription of a target RNA. For example, a target RNA can e.g., due to secondary structure, fail to be reverse transcribed into DNA, or be reverse transcribed at low efficiency in one round or more rounds. In a subsequent round, target RNA can be successfully reverse transcribed due to stochastic reasons.

A round of reverse transcription can be achieved when all, substantially all, a majority of, or at least one RNA in one or more partition mixtures has been transcribed into a first, or a first and second, strand of DNA. Alternatively, a round of reverse transcription can be achieved when all, substantially all, a majority of, or at least one portion of an RNA in one or more partition mixtures has been transcribed into a first, or a first and second, strand of DNA. In some cases, a round of reverse transcription can be initiated when one or more partitions are incubated in the presence of reverse transcriptase, template RNA, one or more suitable primers, buffers, salts, and dNTPs at a temperature and in conditions that are permissive for reverse transcription to occur. A round of reverse transcription that has been initiated can be completed, for example, by employing an extended polymerization step and waiting a sufficient time (e.g., at least 1, 2, 3, 4, 5, 6, 7, 8, 9, 10, 11, 12, 13, 14, 15, 20, 25, 30, 35, 40, 45, 50, 60, 65, 70, 75, 80, or 90 minutes), disrupting a target RNA:reverse transcriptase reaction, utilizing a heat denaturation step, denaturing RNA-DNA hybridization using heat, an enzyme (e.g., a helicase) or a chemical, utilizing a strand displacing reverse transcriptase, or a combination thereof. In some cases, a round of reverse transcription can be completed, when reverse transcription stops and no, or substantially no, more first strand synthesis occurs, or when the first strand and the RNA template are separated.

In some cases, multiple rounds of reverse transcription can be performed by: (1) employing an extended reverse transcription step (e.g., about ½, 1, 1.5, 2, 3, 4, hours or more), (2) disrupting a target RNA:reverse transcriptase reaction (e.g., 1, 2, 3, or more times), (3) utilizing one or more cycles of chemical denaturation or heat denaturation and cooling (e.g., 1, 2, 3, or more times), (4) denaturing RNA-DNA hybridization (e.g., 1, 2, 3, or more times), (5) utilizing a strand displacing polymerase, such as a strand displacing RNA dependent DNA polymerase, (6) addition of other strand displacing enzymes (e.g., a helicase such as Rho) to separate nucleic acid strands, or (7) use of an RNA dependent RNA polymerase to generate multiple RNA complements prior to reverse transcription.

Multiple round reverse transcription can be performed by waiting a sufficient time for all, substantially all, a majority of, or at least one of the reverse transcription enzymes in one or more partition mixtures to perform multiple rounds of DNA synthesis. For example, reverse transcription can be performed for 0.5, 0.75, 1, 1.5, 2, 2.5, 3, 3.5, 4, 4.5, 5, 5.5, 6, 6-7, 7-9, 9-12, 12-16, 16-18, 18-24 hours or more. In some cases, multiple rounds of reverse transcription can be performed when a reverse transcriptase or a DNA polymerase enzyme recognizes a primer bound to an RNA or DNA template, initiates DNA synthesis, disassociates from the template strand and reinitiates synthesis on the same or a different template strand.

In other cases, multiple round reverse transcription is performed by disruption of the target-RNA:reverse transcriptase interaction such that the polymerase dissociates from the strand and is allowed to re-associate and initiate a new round of reverse transcription. In some embodiments, this disruption can be performed by heating one or more partition mixtures. For example, the partition mixtures can be heated to a temperature of greater than about 40°, 50°, 60°, 70°, 80°, 90°, 95°, 97.5°, 98°, or 99° C., for a time greater than about 0.5, 1, 2, 3, 4, 5, 6, 7, 8, 10, 10-15, 15-20, 20-30, 30-45, 45-60 seconds or longer. The interaction can be interrupted by heating 1, 2, 3, 4, 5, 6, 7, 8, 9, 10, or more times. In general, after disruption, the partition mixtures can be cooled back down to an optimal, or near optimal, reaction temperature to undergo subsequent rounds of reverse transcription. In other embodiments, reverse transcription is initiated at one temperature and subsequent rounds are performed at one or more higher temperatures without an intervening cooling step.

In some cases, the first or second round of reverse transcription is terminated by heating to a temperature of greater than about 40°, 50°, 60°, 70°, 80°, 90°, 95°, 97.5°, 98°, or 99° C., for a time greater than about 0.5, 1, 2, 3, 4, 5, 6, 7, 8, 10, 10-15, 15-20, 20-30, 30-45, 45-60 seconds or longer. At least one subsequent round of reverse transcription can then be performed after the sample has been heated and cooled to a temperature of approximately 20°, 22.5°, 25°, 27.5°, 30°, 35°, 40°, 45°, 50°, 55°, 60°, 65°, 70°, 72°, 73°, 74°, or about 75-80° C. The subsequent round(s) can be terminated by heating, chemical denaturant, reversible pH shift, or a combination thereof.

In some cases, a heat resistant enzyme comprising reverse transcriptase activity can be utilized so that after heat disruption, the polymerase activity is substantially retained for multiple rounds. One example of such an enzyme is Tth polymerase which exhibits reverse transcriptase activity in the presence of manganese ions (e.g., about 0.1, 0.3, 0.4, 0.5, 0.6, 0.7, 0.8, 0.9, 1.0, 1.1, 1.2, 1.5, 1.75, 2, 2.5, 3, 4, or 5 mM manganese). In other cases, polymerase activity can be reduced in subsequent rounds of reverse transcription (e.g. due to time, heat, or reaction conditions), and yet still be capable of sufficient reverse transcriptase activity. In yet other cases, a partition mixture can comprise a mixture of reverse transcriptase and hot-start reverse transcriptase such that a first round of reverse transcription is performed, the sample is heated—inactivating a portion of the reverse transcriptase and activating some or all of the hot-start reverse transcriptase—and further rounds of reverse transcription are performed, mediated by the hot start reverse transcriptase. Methods for generating and using hot-start polymerases are known in the art. For example, a polymerase can be bound to an inhibitory antibody or other molecule (e.g. a protein-based inhibitor) that is heat labile. Heating of the polymerase: inhibitor complex can then release active polymerase.

In other embodiments, multiple rounds of reverse transcription can be performed in a set of partition mixtures by disrupting the RNA-DNA hybridization. For example, a helicase can be incorporated into the reaction mixture to separate the strands. In some cases, a helicase can be added to the partition mixtures after one or more initial rounds of reverse transcription. Exemplary helicases include, but are not limited to, Rho.

In some embodiments, multiple rounds of reverse transcription can be performed in a set of partition mixtures by utilizing chemical denaturation to disrupt the RNA-DNA hybridization, or to disrupt the polymerase-nucleic acid interaction. For example, samples can be partitioned, reverse transcription performed in the partitions, denaturant added to the partitions, denaturant removed or diluted sufficiently, and one or more additional rounds of reverse transcription performed. In some cases, the additional rounds of reverse transcription can be performed using re-natured polymerase, additional polymerase can be added to the droplets, or a combination thereof. Chemical denaturants include but are not limited to an acid, a base, urea, guanidine hydrochloride, a solvent (e.g., methanol, ethanol, isopropanol, dimethylsulfoxide, formamide, dimethylformamide, N-Methyl-2-pyrrolidone, glycerol, ethylene glycol, 1,2 propanediol, etc.), a salt (e.g., NaCl, KCl, MgCl, $MnCl_2$, tetramethylammonium chloride, or a hydrate thereof), a sulfoxide or sulfone (e.g., methyl sulfone, methyl sec-butylsulfoxide, n-propyl sulfoxide, n-butylsulfoxide, and tetramethylene sulfoxide, etc.), betaine (e.g., trimethylglycine), a non-ionic detergent (e.g., polyoxyethylenesorbitan monolaurate, nonyl phenoxypolyethoxylethanol, octyl phenoxypolyethoxylethanol, polyoxyethylene octyl phenyl ether, etc.), or an ionic detergent (e.g., sodium dodecyl sulfate, sarkosyl, etc.).

In another embodiment, multiple rounds of reverse transcription of a target RNA molecule can be performed in a set of partition mixtures by altering the pH of the reaction mixture. For example, the pH of the reaction mixture may be raised or lowered such that an RNA-DNA hybrid is denatured, or an RNA-Dependent DNA polymerase is denatured. Subsequently, the pH shift may be partially or completely reversed to permit reverse transcription to resume. In some embodiments, the pH is shifted and reversed multiple times (e.g., 1, 2, 3, 4, 5, 6, 7, 8, 9, 10 or more times) to provide multiple rounds of reverse transcription. The pH shift may be provided by any suitable method known in the art such as, for example, the addition of one or more acid or base to the droplet. In some cases, a pH shift can be induced by the application of light. For example, a light-sensitive dye in the reaction mixture may be illuminated at one or more wavelengths of light suitable for causing the pH of the mixture to shift. The pH shift may subsequently be reversed by removal of the illumination, or alteration of the wavelength of illumination. Examples of such light-sensitive dyes are provided in the following table:

| Dye | pH Range | pKa | Wavelength |
| --- | --- | --- | --- |
| Thymolsulfonphthalein | 1.2-2.8 | 1.65 | 544-430 |
| Tetrabromophenol-sulfonphthalein | 3.0-4.6 | 4.10 | 436-592 |
| Dimethylaminoazobenzene-p-sulfonate | 3.1-4.4 | 3.46 | 522-464 |
| Tetrabromo-m-cresol-sulfonphthalein | 3.8-5.4 | 4.90 | 444-617 |
| Dimethylaminoazobenzene-o-carboxylic acid | 4.2-6.3 | 5.00 | 444-617 |
| Dibromo-o-cresol-sulfonphthalein | 5.2-6.8 | 6.40 | 433-591 |
| Dibromothymolsulfo-phthalein | 6.2-7.6 | 7.30 | 433-617 |
| Phenolsulfonphthalein | 6.8-8.4 | 8.00 | 433-558 |
| o-Cresolsulfonphthalein | 7.2-8.8 | | 434-572 |
| Thymolsulfonphthalein | 8.0-9.6 | 9.20 | 430-596 |
| Di-p-dioxydiphenyl-phthalide | 8.3-10.0 | | 553 |

In yet another embodiment, multiple rounds of reverse transcription of a target RNA molecule can be performed in a set of partition mixtures by a combination of a chemical denaturant and heat, or a combination of a reversible pH shift and heat, or a combination of reversible pH shift and chemical denaturant. For example, a chemical denaturant such as acid, base, salt, solvent, or detergent may be present in a partition mixture such that, at a permissive temperature, it does not substantially interfere with reverse transcription. Subsequently, the temperature may be raised to a non-permissive temperature to denature RNA-DNA hybrids in the partition mixture or cause the reverse transcriptase to dissociate from the template molecule. In some cases, the non-permissive temperature is lower due to the presence of the chemical denaturant. The temperature may then be lowered to a permissive temperature to allow a subsequent round of reverse transcription to occur.

In another example, the pH may be reversibly shifted in a partition mixture and the temperature raised to a non-permissive temperature to denature RNA-DNA hybrids and/or the reverse transcriptase. The pH shift may then be reversed and the temperature lowered to effect multiple rounds of reverse transcription. In some cases, the non-permissive temperature is lowered by the reversible pH shift. In yet another example, a chemical denaturant such as acid, base, salt, solvent, or detergent may be present in a partition mixture such that, at a given temperature, it does not substantially interfere with reverse transcription. Subsequently, the pH may be reversibly shifted to a non-permissive pH to denature RNA-DNA hybrids and/or the reverse transcriptase. The pH shift may then be partially or completely reversed to effect multiple rounds of reverse transcription. In some cases, the difference between the non-permissive pH and the permissive pH is smaller due to the presence of the chemical denaturant.

In another embodiment, multiple rounds of reverse transcription of a target RNA molecule can be performed in a set of partition mixtures by utilizing a reversibly inactivated reverse transcriptase. Examples of reversibly inactivated reverse transcriptases can be found in United States Patent Application Publication 2011/0159551, incorporated herein by reference. In this embodiment, reverse transcription can be performed at a permissive temperature (e.g., about 30, 35, 37, 40, 42, 45, 47, 50, 55, 60° C. or more). The temperature can then be lowered to a non-permissive stop reverse transcription (e.g. about 37, 35, 30, 27, 25, 22, 20, 17, 15, 10, 5, 4, 0° C., or less). The partition mixture can optionally be incubated at the non-permissive temperature for a sufficient time to allow a majority of the reverse transcriptase molecules in a set of partitions to fall off the template strand. Finally, the temperature can be raised to a permissive temperature to effect multiple rounds of reverse transcription. In some cases, multiple rounds of reverse transcription can be performed by employing a reversibly inactivated reverse transcriptase in a set of partition mixtures in combination with a chemical denaturant or a reversible pH shift.

In yet another embodiment, multiple rounds of reverse transcription of a target RNA molecule can be performed in a set of partition mixtures via a rolling circle mechanism. In some cases, the rolling circle mechanism can be performed by incorporating an RNA ligase in a partition mixture to circularize the target RNA molecule. The circularized target RNA molecule will thus serve as a continuous template for multiple rounds of first strand DNA synthesis. In some cases, an RNA-dependent DNA polymerase with strand displacement activity can be utilized to provide multiple rounds of first strand DNA synthesis from a circular RNA template.

Figure 2:
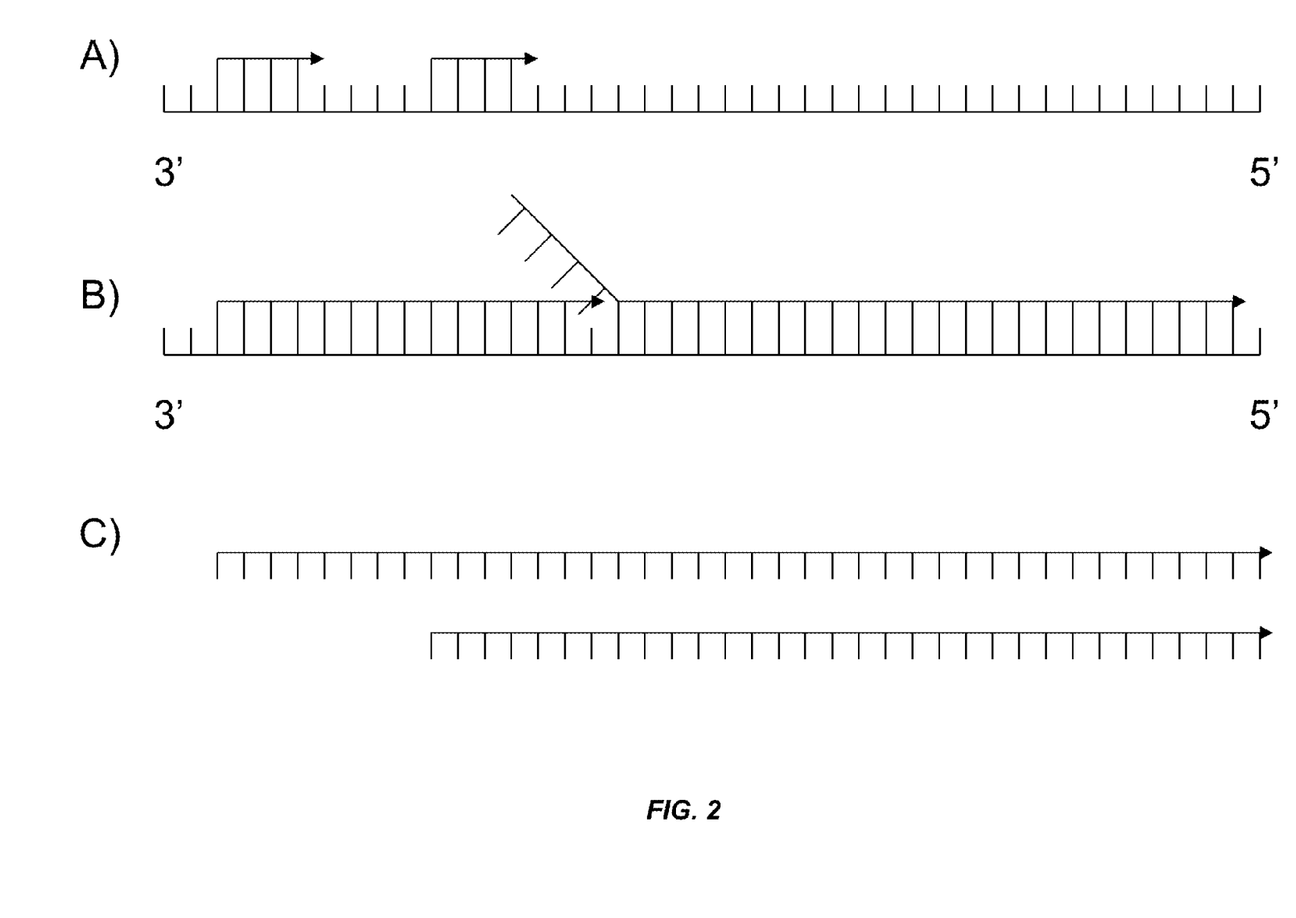
FIG. 2, illustrates a use of tandemly arrayed primers for multiple first strand syntheses. A) Tandemly arrayed primers bind to RNA template strand. B) During extension, the polymerizing strand initiated with the oligonucleotide located closer to the 3' end of the template RNA begins displacing the strand initiated by the oligonucleotide located closer to the 5' end of the template RNA. C) After extension is complete, the tandemly arrayed oligos generate one cDNA strand per each tandemly arrayed oligo.

In yet another embodiment, a strand displacing reverse transcriptase can be coupled with tandemly arrayed primers such that a first tandemly arrayed primer initiates first strand synthesis in the 3' direction and a second tandemly arrayed primer also initiates first strand synthesis in the 3' direction, wherein the first tandemly arrayed primer hybridizes at a position on the template RNA that is 5' of the second tandemly arrayed primer. (FIG. 2) Thus, the synthesis of the first strand from the second tandemly arrayed primer displaces the first strand from the first tandemly arrayed primer. In some cases the tandemly arrayed primers comprise random sequences. In other cases, the tandemly arrayed primers comprise specific sequences.

In yet another embodiment, multiple cDNA strands from one RNA template are generated using a composite primer based linear amplification method, e.g., as described in U.S. Pat. No. 6,946,251. In certain aspects, multiple cDNA strands (e.g., double or single stranded cDNA) are each generated from a plurality of template molecules, wherein the plurality of template molecules are partitioned during the linear amplification step. In some aspects, multiple cDNA strands (e.g., double or single stranded cDNA) are each generated from a plurality of template molecules, wherein the plurality of template molecules are partitioned, barcoded, recombined, and amplified by linear amplification. As described herein, the plurality of template molecules can be partitioned so that there is less than about 0.1, 0.2, 0.4, 0.5, 0.75, or less than about 1 template molecule per partition. Thus, bias among different RNA template molecules can be avoided. By way of explanation, and without wishing to be bound by theory, the referenced linear amplification requires comparable amplification efficiency among targets when performed in bulk in order to avoid bias. In partitions, this requirement is no longer critical. If one target generates more cDNA than another, the correct concentration measurements can still be performed. In some cases, so long as at least one cDNA is made from each template correct absolute or relative concentrations of the starting RNA templates can be obtained.

b. Reverse Transcriptases and Polymerases

Methods are provided herein for both first- and second-strand cDNA synthesis. In some cases, first and second strand cDNA is produced by reverse transcription, wherein a first strand of DNA is made from RNA using a reverse transcriptase which comprises RNA-dependent DNA polymerase activity and a second strand of DNA is made using reverse transcriptase which comprises DNA-dependent DNA polymerase activity. In other embodiments, the first strand is produced by reverse transcription (e.g. using a reverse transcriptase), and the second strand is produced by another enzyme (e.g. a DNA-dependent DNA polymerase). Reverse transcriptases are found in all retroviruses and are commonly obtained from avian myeloblastoma virus or Moloney murine leukemia virus; enzyme from these sources is commercially available from Life Technologies (Gaithersburg, Md.) and Boehringer Mannheim (Indianapolis, Ind.).

In some embodiments, catalytic activities such as an RNA-dependent DNA polymerase activity, an RNaseH activity, and a DNA-dependent DNA polymerase activity are employed to convert a primer-RNA hybrid to double-stranded cDNA. Most reverse transcriptases, including those derived from Moloney murine leukemia virus (MMLV-RT), avian myeloblastosis virus (AMV-RT), bovine leukemia virus (BLV-RT), Rous sarcoma virus (RSV) and human immunodeficiency virus (HIV-RT) catalyze each of these activities. These reverse transcriptases are sufficient to convert a primer-RNA hybrid to double-stranded DNA in the presence of additional reagents that include, but are not limited to: dNTPs; monovalent and divalent cations, e.g., $KCl_2$; $MgCl_2$; sulfhydryl reagents, e.g., dithiothreitol; and buffering agents, e.g., Tris-Cl. Alternatively, a variety of proteins that catalyze one or two of these activities can be added to a cDNA synthesis reaction. For example, MMLV reverse transcriptase lacking RNaseH activity (described in U.S. Pat. No. 5,405,776) catalyzes RNA-dependent DNA polymerase activity and DNA-dependent DNA polymerase activity. These proteins can be added together during a single reaction step, or added sequentially during two or more sub steps.

In one embodiment, first-strand cDNA synthesis is allowed to proceed at a lower temperature (for example, 25° C.) for a certain period of time (e.g., 10 min) prior to increasing the temperature (e.g., to 40° C.) for the remainder of the reverse transcription reaction, which improves annealing of the first primer to its target nucleic acid sequence. This type of two-step reaction can be referred to in the art as "cyclic reverse transcription" (See, e.g., US Patent Publication No. 2010/0221786, herein incorporated by reference). In some embodiments, such cyclic reverse transcription can be performed multiple times (e.g. at least 2, 3, 4, 5, 6, 7, 8, 9, 10, etc. times). For example, a first strand cDNA synthesis can be allowed to proceed for a time at a lower temperature, and the temperature can be increased for the remainder of the round of reverse transcription. In another round, first strand synthesis can be allowed again to proceed at a lower temperature, and the temperature then increased for completion of another round. In other cases, one or more rounds of reverse transcription can be performed using a lower and then a higher temperature, and one or more rounds can be performed at a single temperature.

Additional proteins that can enhance the yield of DNA product can also be added to the cDNA synthesis reaction. These proteins include a variety of DNA polymerases (such as those derived from E. coli, thermophilic bacteria, archaebacteria, phage, yeasts, Neurosporas, Drosophilas, primates and rodents), DNA ligases (such as those derived from phage or cellular sources, including T4 DNA ligase and E. coli DNA ligase), and nucleic acid binding proteins (such as single stranded DNA binding protein). Other proteins that can enhance the yield of DNA product include proteins which reduce non-specific binding or adsorption, or cause molecular crowding such as BSA, lysozyme, ovalbumin, ubiquitin, or any suitable protein.

Similarly, additives can be included in the methods provided herein to increase the efficiency of the reverse transcription reaction or subsequent amplification. For example, a chemical denaturant can be included during DNA polymerization (e.g., during first or second strand cDNA synthesis, or during amplification) at a concentration sufficient to inhibit nucleic acid secondary structure formation, or reduce non-specific priming. In some cases, the concentration of chemical denaturant does not substantially inhibit one or more polymerases (e.g., reverse transcriptase or DNA polymerase).

Chemical denaturants include but are not limited to an acid, a base, urea, guanidine hydrochloride, a solvent (e.g., methanol, ethanol, isopropanol, dimethylsufoxide, formamide, dimethylformamide, N-Methyl-2-pyrrolidone, glycerol, ethylene glycol, 1,2 propanediol, etc.), a salt (e.g., NaCl, KCl, MgCl, $MnCl_2$, tetramethylammonium chloride, or a hydrate thereof), a sulfoxide or sulfone (e.g., methyl sulfone, methyl sec-butylsulfoxide, n-propyl sulfoxide, n-butylsulfoxide, and tetramethylene sulfoxide, etc.), betaine (e.g., trimethylglycine), a non-ionic detergent (e.g., polyoxyethylenesorbitan monolaurate, nonyl phenoxypoly-ethoxylethanol, octyl phenoxypolyethoxylethanol, polyoxy-ethylene octyl phenyl ether, etc.), or an ionic detergent (e.g., sodium dodecyl sulfate, sarkosyl, etc.). Other additives that can be employed to increase the efficiency of reverse transcription or subsequent amplification include molecular crowding agents such as polysucrose, polyethylene glycol, dextran, and polyvinylpyrrolidone.

Depending on the particular protocol, the same or different DNA polymerases can be employed during the cDNA synthesis steps. In one embodiment, a single reverse transcriptase, e.g., MMLV-RT, can be utilized as a source of all activities for converting the primer-mRNA hybrid to double-stranded cDNA. In another embodiment, the polymerase employed in first strand cDNA synthesis is different from that which is employed in second strand cDNA synthesis. Specifically, a reverse transcriptase lacking RNaseH activity (e.g., SUPERSCRIPT II™) can be combined with the primer-mRNA hybrid during a first sub step for first strand synthesis. A source of RNaseH activity, such as *E. coli* RNaseH or MMLV-RT, can then be added during a second sub step to initiate second strand synthesis.

In yet other embodiments, the requisite activities are provided by a plurality of distinct enzymes. For example, some embodiments use MMLV-RT, or a combination of SUPERSCRIPT II™ and MMLV-RT, or a combination of SUPERSCRIPT II™ and *E. coli* RNaseH, for cDNA synthesis. In any of the methods of the present invention, reagents, such as enzymes, including reverse transcriptase or DNA polymerase can be added to a partition mixture at any time by fusing partition mixture droplets with a liquid or another partition mixture containing the reagent to be added, by flowing a liquid into partition mixtures in one or more micro channels, or by lysing an internal droplet inside the partition mixture to release the contents of the droplet.

c. Primers for cDNA Synthesis

In some embodiments, the primer for first strand cDNA synthesis is a mixture of random primers that prime synthesis in a direction toward the 5' end of the nucleic acids (e.g., mRNAs) in the sample, and the primer for second strand cDNA synthesis is a mixture of random primers that prime synthesis of double-stranded cDNA from all, substantially all, a majority of, or at least some of the first strand cDNAs thus produced. In other embodiments, the primer for the first strand cDNA synthesis is an oligo-dT primer that primes the synthesis of DNA in a direction toward the 5' end of the target nucleic acid (e.g. mRNA) in the sample, and the primer for the second strand is a mixture of random primers that prime synthesis of double-stranded cDNA from all, substantially all, a majority of, or at least some of the first strand cDNAs thus produced. In yet other embodiments, the primer for the first strand cDNA synthesis is a mixture of random primers and oligo-dT primers. In particular embodiments the poly-dT sequence comprises at least 5 thymidilate residues, 15 to 25 residues, or 18 thymidilate residues in length.

In some cases, random primers include primers that comprise a random (poly-dN) sequence of 6-9 nucleotides. In some cases, a random nucleotide includes an A, a G, a C, or a T. In some cases, other bases can be incorporated into the primers that bind to more than one of A, G, C, or T as a complementary base, including for example, inosine, 5-nitroindole, 3-nitropyrrole, 3,4-dihydropyrimido[4,5-c][1,2]oxazin-7-one, or N6-methoxy-2,6-diaminopurine.

Typically, the poly-dN region is sufficiently long to provide for efficient hybridization to the target RNA, where the region ranges in length from, for example, 4-50 nucleotides in length, 6-25 nucleotides in length, from 6-12, or 9 nucleotides in length, i.e., a random 9-mer. In specific embodiments, the poly-dN region is 4, 5, 6, 7, 8, 9, 10, 11, or 12 nucleotides in length. In another embodiment, the random primers used to prime first strand cDNA synthesis are a complete set of all (or almost all) combinations of random 9-mers, i.e., a total of $4^9$ 9-mers.

In some embodiments, the primer for second strand cDNA synthesis is a mixture of primers consisting of a poly-dN sequence that is sufficiently long to provide for efficient hybridization to the mRNA. The sequence can range in length from 4-50, 6-25, 6-12, 6-9, or 6 degenerate bases, i.e., a random hexamer (dN6), wherein the degenerate bases can be A, T, G, or C. In theory, the primer should hybridize on average $4^6$ or 4096 base pairs from the 3' priming site of the first-strand cDNA. In specific embodiments, the poly-dN sequence is 4, 5, 6, 7, 8, 9, 10, 11, or 12 nucleotides in length. In a specific embodiment, the random primers used to prime second strand cDNA synthesis will be a complete set of all combinations of random hexamers, i.e., a total of $4^6$ or 4096 hexamers.

In some cases random primers can comprise primers having a random residue present in each position of the 3' end sequence or in each position of a 3' portion of the primer. In some cases, the primers can further comprise a barcode or other detectable sequence or label at or near the 5' end of the primer. In some cases, the primers can comprise random nucleotides at or near the 3' portion of the primer, a barcode, and another detectable sequence or label. In other cases, a primer can comprise an oligo-dT region at or near a 3' portion of the primer and a barcode or other detectable sequence or label at or near the 5' portion of the primer. A linker oligonucleotide between the priming region (e.g. the random or oligo-dT portion) and a barcode or other detectable sequence or label can be present, and if, present, will typically comprise between about 5 and 20 bases, but can be smaller or larger as desired.

As used herein a "barcode" is a short nucleotide sequence (e.g., at least about 4, 6, 8, 10, or 12, nucleotides long) that uniquely defines a cDNA molecule, or a cDNA generated in a particular partition. For example, partitions containing target RNA can be reverse transcribed using primers that contain a different barcode sequence in each partition, thus incorporating a unique barcode into the reverse transcribed nucleic acids of each partition. Partitions can then be combined, and optionally amplified, without losing track of which partitions contained which reverse transcribed RNA. Thus, presence or absence of a reverse transcribed nucleic acid comprising each barcode can be counted (e.g. by sequencing) without the necessity of maintaining physical partitions. The length of the barcode sequence determines how many unique samples can be differentiated. For example, a 4 nucleotide barcode can differentiate $4^4$ or 256 samples or less, a 6 nucleotide barcode can differentiate 4096 different samples or less, and an 8 nucleotide barcode can index 65,536 different samples or less. Additionally, barcodes can be attached to both strands either through barcoded primers for both first and second strand synthesis or through ligation. The use of two distinct barcodes on the two strands increases the number of independent events that can be distinguished. Alternatively, the same barcode can be attached to the first and second strand. The use of the same barcode, e.g., by incorporating the same barcode in primers for both the first and second strand synthesis in each partition can result in identical barcodes on both strands. The dual barcoding can provide a check against subsequent detection errors such as sequencing or amplification errors confounding downstream analysis and allow detection of either or both strands without compromising quantification. The use of barcode technology is well known in the art, see for example Katsuyuki Shiroguchi, et al. *Digital RNA sequencing minimizes sequence-dependent bias and amplification noise with optimized single-molecule barcodes*, PNAS (2012); and Smith, A M et al. *Highly-multiplexed barcode sequencing: an efficient method for parallel analysis of pooled samples*, Nucleic Acids Research Can 11, (2010).

In some cases, primers are selected for first and/or second strand cDNA synthesis that are target specific, or are designed to hybridize to a limited number of target nucleic acid sequences. For example, the first strand primer can be selected to hybridize to a single RNA sequence and direct synthesis of first strand DNA from that sequence. Alternatively, the first strand primer can be selected to hybridize to a set of related RNA sequences. For example, the first strand primer can be selected to hybridize, and direct DNA synthesis of, a family of receptor tyrosine kinases. In some cases, the first strand primer can be designed to hybridize to a conserved region of a family of related sequences. Similarly, the second strand primer can be designed to hybridize to a specific sequence of first strand DNA, or a family of related sequences. Specific primers can also be designed to include sequences or markers that can be used as barcodes as previously noted. However, the term "specific primers" does not imply one set of primers per target. In some cases, multiple primer sets targeting essentially the same locus may be combined with one or more primer sets targeting other loci. For example, tandemly arrayed primers that result in similar, but not identical, first or second strand products for one locus can be multiplexed with primers that target other loci.

In some embodiments, the methods of the present invention may utilize a combination of random or oligo-dT primers and target specific primers. For example, random primers may be utilized to reverse transcribe all, substantially all, or a majority of the RNA molecules present in a partition mixture, and target specific primers may be utilized to ensure reverse transcription of specific sequences. In other cases, specific primers can be used without the addition of random or oligo dT primers.

In some cases, more than one set of primers are selected for first and/or second strand cDNA synthesis that are target specific. Combining multiple sets of specific primers (multiplexing primer sets) for first strand and/or second strand synthesis presents challenges known to those skilled in the art. One particular issue that arises when multiplexing specific primers, is the loss of accurate quantification among the targets because different targets are reverse transcribed at different efficiencies. This may result in inaccurate estimation of target molecules. Indeed, in a bulk reaction, multiplex RNA quantification relies on the assumption that reverse transcription will occur with substantially equal efficiency across the different target molecules. An assumption that often proves false. In contrast, by quantifying target RNA molecules in a set of partition mixtures using multiple rounds of reverse transcription, partitions are counted as containing a target molecule whether one or more copies of the target molecule are available for subsequent detection. Therefore, methods of the present invention do not rely on the assumption that reverse transcription is equally efficient, or substantially so, across different target molecules. As long as the efficiency of the reverse transcription reaction is sufficient to generate at least one template for subsequent detection after all rounds of reverse transcription are completed, the quantification will be maintained.

The first and second strand primers can additionally contain a restriction site. Restriction enzymes and the sites they recognize can be found, for example, in Sambrook et al., 1989, Molecular Cloning-A Laboratory Manual (2nd Ed.), Vol. 1, Chapter 5, Cold Spring Harbor Laboratory, Cold Spring Harbor, N.Y.

III. Samples

Methods, compositions, and kits are provided to detect one or more target RNA molecules, such as an mRNA or an mi-RNA, in any type of sample. In some embodiments, the sample is a biological sample. Biological samples can be obtained from any biological organism, e.g., an animal, plant, fungus, bacterial, or any other organism. In some embodiments, the biological sample is from an animal, e.g., a mammal (e.g., a human or a non-human primate, a cow, horse, pig, sheep, cat, dog, mouse, or rat), a bird (e.g., chicken), or a fish. A biological sample can be any tissue or bodily fluid obtained from the biological organism, e.g., blood, a blood fraction, or a blood product (e.g., serum, plasma, platelets, red blood cells, and the like), sputum or saliva, tissue (e.g., kidney, lung, liver, heart, brain, nervous tissue, thyroid, eye, skeletal muscle, cartilage, or bone tissue); cultured cells, e.g., primary cultures, explants, and transformed cells, stem cells, stool, urine, etc.

The number of copies of the target RNA in a sample to be analyzed can be 0, or about or at least about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 2000, 3000, 4000, 5000, 6000, 7000, 8000, 9000, 10,000, 20,000, 30,000, 40,000, or 50,000. In some embodiments, the sample comprises a low concentration and/or copy number of the one or more target RNA(s). In some cases, the target nucleic acid is difficult to transcribe because it is present at a very low concentration. For example, one or more of the target RNA(s) may be present at nanomolar, picomolar, femtomolar, attomolar, or lower concentrations in the sample. As another example, one or more of the target RNA(s) may be present in the sample at a frequency of about $10^9$, $10^6$, or $10^3$ target RNA molecules per microliter of sample, or less. In some embodiments, one or more of the target RNA(s) may be present in the sample at a frequency of about 900, 800, 700, 600, 500, 400, 300, 200, or 100 target RNA molecules per microliter of sample, or less. In some embodiments, one or more of the target RNA(s) may be present in the sample at a frequency of about 10, 9, 8, 7, 6, 5, 4, 3, 2, 1, 0.5, 0.1, 0.05 target RNA molecules per microliter of sample, or less.

In some embodiments, the sample can be prepared to improve the efficient detection of a target molecule or molecules (e.g., a target RNA molecule or molecules such as one or more mRNA molecules). For example, the sample can be purified, fragmented, fractionated, homogenized, or sonicated. In some embodiments, an RNA molecule or molecules of interest, or a sub-fraction comprising the RNA molecule or molecules of interest, can be extracted or isolated from a sample (e.g., a biological sample). In some embodiments, the sample is enriched for the presence of the one or more RNA molecules. In some embodiments, the RNA molecule is enriched in the sample by an affinity method, e.g., immunoaffinity enrichment. In some embodiments, the RNA molecule is enriched in the sample using size selection (e.g., removing very small fragments or molecules or very long fragments or molecules). In other embodiments, the RNA molecule is enriched by selecting for the poly-A tail of eukaryotic messenger RNA. For example, the sample can be passed over an oligo-dT column, and poly-A enriched RNA can be eluted for further analysis.

In some embodiments, the sample is maintained at a controlled temperature or range of temperatures before, during, and/or after partitioning the sample. In some embodiments, the sample is maintained at a temperature of about 20°, 25°, 30°, 35°, 40°, 45°, 50°, 55°, 60°, 65°, 70°, 75°, 80°, 85°, 90°, or 95° C. before, during, and/or after partitioning the sample, e.g., at a temperature to allow for amplification of signal generated by one or more labeled probes.

In some embodiments, the sample contains one or more target nucleic acids that are difficult to reverse transcribe. For example, the sample may contain one or more target nucleic acids that are prone to secondary structure formation. In some cases, the target may be difficult to transcribe due to a high GC or AT content (e.g., greater than about 55, 60, 65, 70, 75, 80, 85, 90, 95, 99%, or more GC or AT content). In some cases, primers that hybridize to the target nucleic acid may be prone to secondary structure formation. In other cases, the target nucleic acid may contain repetitive sequences, or sequences of low complexity. In other cases, primers that initiate reverse transcription, or amplification of the reverse transcription product may hybridize non-specifically to other sequences. In some cases, the non-specific hybridization is due to the presence of similar sequences in the sample.

Target nucleic acids of the present invention that are prone to secondary structure include RNA molecules that have a secondary structure melting temperature of greater than about 25, 27.5, 30, 32.5, 35, 37.5, 40, 42.5, 45, 47.5, 50, 52.5, 55, 57.5, 60° C. or more. For example, a target molecule of the present invention that is difficult to reverse transcribe can contain a stem-loop structure with a melting point greater than about 25, 27.5, 30, 32.5, 35, 37.5, 40, 42.5, 45, 47.5, 50, 52.5, 55, 57.5, 60° C. or more. In some cases, a target molecule may be difficult to transcribe because it retains significant secondary structure at the permissive temperature for the reverse transcription reaction. For example, 25%, 30%, 35%, 40%, 45%, 50%, 55%, 60%, 65%, 70%, 75%, 80%, 85%, 90%, 95%, 99% or more of one or more of the target molecules in the sample may retain secondary structure at a temperature that is otherwise permissive for reverse transcription (e.g., at a temperature at which the reverse transcriptase enzyme is active and primers are generally expected to hybridize).

Low complexity regions represent sequences of very non-random composition ('simple sequences', 'compositionally-biased regions'). They are abundant in natural sequences. Low complexity regions can be found by manual inspection or with the aid of a computer program. For example, the program TANTAN (Frith, M. C., *Nucleic Acids Res.* 2011 March; 39(4):e23.) can be used to identify low complexity regions.

IV. Partitioning of the Sample

The sample comprising the one or more target RNA molecules to be detected can be partitioned into a plurality of partitions. Partitions can include any of a number of types of partitions, including solid partitions (e.g., wells or tubes) and fluid partitions (e.g., aqueous droplets within an oil phase). In some embodiments, the partitions are droplets. In some embodiments, the partitions are micro channels. Methods and compositions for partitioning a sample are described, for example, in published patent applications WO 2010/036352, US 2010/0173394, US 2011/0092373, and US 2011/0092376, the entire content of each of which is incorporated by reference herein.

In some embodiments, reagents such as target nucleic acid, buffers, enzymes, substrates, nucleotides, salts, etc. are mixed together prior to partitioning, and then the sample is partitioned. In some cases, the sample is partitioned shortly after mixing reagents together so that substantially all, or the majority, of reverse transcription occurs after partitioning. In other cases, the reagents are mixed at a temperature in which reverse transcription proceeds slowly, or not at all, the sample is then partitioned, and the reaction temperature is adjusted to allow the reverse transcription reaction to proceed. For example, the reagents can be combined on ice, at less than 5° C., or at 0, 1, 2, 3, 4, 5, 6, 7, 8, 9, 10, 11, 12, 13, 14, 15, 16, 17, 18, 19, 20, 20-25, 25-30, or 30-35° C. or more. In general, one of skill in the art will know how to select a temperature at which the one or more reverse transcriptase enzymes are not active. In some cases, a combination of temperature and time are utilized to avoid substantial reverse transcription prior to partitioning.

Additionally, reagents can be mixed using one or more hot start enzymes, such as a hot start reverse transcriptase. Thus, target RNA, buffers, salts, nucleotides, labels, enzymes, etc. can be mixed and then partitioned. Subsequently, the reverse transcription reaction, including multiple rounds of reverse transcription, can be initiated by heating the partition mixtures to activate the one or more hot-start enzymes.

Additionally, reagents can be mixed together without one or more reagents necessary to initiate the reverse transcription reaction. The mixture can then be partitioned into a set of first partition mixtures and then the one or more essential reagents can be provided by fusing the set of first partition mixtures with a set of second partition mixtures that provide the essential reagent. Alternatively, the essential reagent can be added to the first partition mixtures without forming second partition mixtures. For example, the essential reagent can diffuse into the set of first partition mixture water-in-oil droplets. As another example, the missing reagent can be directed to a set of micro channels which contain the set of first partition mixtures.

In some embodiments, the sample is partitioned into a plurality of droplets. In some embodiments, a droplet comprises an emulsion composition, i.e., a mixture of immiscible fluids (e.g., water and oil). In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets described herein are relatively stable and have minimal coalescence between two or more droplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9%, or 10% of droplets generated from a sample coalesce with other droplets. The emulsions can also have limited flocculation, a process by which the dispersed phase comes out of suspension in flakes.

In some embodiments, the droplet is formed by flowing an oil phase through an aqueous sample comprising the target molecule(s) to be detected. In some embodiments, the aqueous sample comprising the target molecule(s) to be detected further comprises a buffered solution and two or more probes for detecting the target molecule(s).

The oil phase can comprise a fluorinated base oil which can additionally be stabilized by combination with a fluorinated surfactant such as a perfluorinated polyether. In some embodiments, the base oil comprises one or more of a HFE 7500, FC-40, FC-43, FC-70, or another common fluorinated oil. In some embodiments, the oil phase comprises an anionic fluorosurfactant. In some embodiments, the anionic fluorosurfactant is Ammonium Krytox (Krytox-AS), the ammonium salt of Krytox FSH, or a morpholino derivative of Krytox FSH. Krytox-AS can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.50%, 1.75%, 2.0%, 2.25%, 2.5%, 2.75%, or 3.0% (w/w). In some embodiments, 1H,1H,2H,2H-Perfluorodecanol is added to a concentration of about 0.18% (w/w).

In some embodiments, the emulsion is formulated to produce highly monodisperse droplets having a liquid-like interfacial film that can be converted by heating into microcapsules having a solid-like interfacial film; such microcapsules can behave as bioreactors able to retain their contents through an incubation period. The conversion to microcapsule form can occur upon heating. For example, such conversion can occur at a temperature of greater than about 40°, 50°, 60°, 70°, 80°, 90°, or 95° C. During the heating process, a fluid or mineral oil overlay can be used to prevent evaporation. Excess continuous phase oil can or can not be removed prior to heating. The microcapsules can be resistant to coalescence and/or flocculation across a wide range of thermal and mechanical processing.

Following conversion, the microcapsules can be stored at about −70°, −20°, 0°, 3°, 4°, 5°, 6°, 7°, 8°, 9°, 10°, 15°, 20°, 25°, 30°, 35°, or 40° C. In some embodiments, these capsules are useful for storage or transport of partition mixtures. For example, samples can be collected at one location, partitioned into droplets containing enzymes, buffers, and/or primers, optionally one or more reverse transcription reactions can be performed, the partitions can then be heated to perform microencapsulation, and the microcapsules can be stored or transported for further analysis.

The microcapsule partitions can contain one or more probes (e.g., labeled probes as described herein) and can resist coalescence, particularly at high temperatures. Accordingly, the capsules can be incubated at a very high density (e.g., number of partitions per unit volume). In some embodiments, greater than 100,000, 500,000, 1,000,000, 1,500,000, 2,000,000, 2,500,000, 5,000,000, or 10,000,000 partitions can be incubated per mL. In some embodiments, the sample-probe incubations occur in a single well, e.g., a well of a microtiter plate, without inter-mixing between partitions. The microcapsules can also contain other components necessary for the incubation.

In some embodiments, the sample is partitioned into at least 500 partitions, at least 1000 partitions, at least 2000 partitions, at least 3000 partitions, at least 4000 partitions, at least 5000 partitions, at least 6000 partitions, at least 7000 partitions, at least 8000 partitions, at least 10,000 partitions, at least 15,000 partitions, at least 20,000 partitions, at least 30,000 partitions, at least 40,000 partitions, at least 50,000 partitions, at least 60,000 partitions, at least 70,000 partitions, at least 80,000 partitions, at least 90,000 partitions, at least 100,000 partitions, at least 200,000 partitions, at least 300,000 partitions, at least 400,000 partitions, at least 500,000 partitions, at least 600,000 partitions, at least 700,000 partitions, at least 800,000 partitions, at least 900,000 partitions, at least 1,000,000 partitions, at least 2,000,000 partitions, at least 3,000,000 partitions, at least 4,000,000 partitions, at least 5,000,000 partitions, at least 10,000,000 partitions, at least 20,000,000 partitions, at least 30,000,000 partitions, at least 40,000,000 partitions, at least 50,000,000 partitions, at least 60,000,000 partitions, at least 70,000,000 partitions, at least 80,000,000 partitions, at least 90,000,000 partitions, at least 100,000,000 partitions, at least 150,000,000 partitions, or at least 200,000,000 partitions.

In some embodiments, the sample is partitioned into a sufficient number of partitions such that at least a majority of partitions have no more than 5, 4, 3, 2, 1, or 0 copies of the target molecule. In some embodiments, a majority of the partitions have no more than 5, 4, 3, 2, 1, or 0 copies of the one or more target molecules to be detected. In some embodiments, on average no more than 5, 4, 3, 2, 1, 0.5, 0.1, 0.05, 0.01, 0.005, 0.001, or fewer copies of the one or more target molecules are present in each partition. In some embodiments, on average about 0.001, 0.005, 0.01, 0.05, 0.1, 0.2, 0.5, 1, 2, 3, 4, or 5 copies of the target molecule are present in each partition. In some embodiments, on average about 0.001, 0.005, 0.01, 0.05, 0.1, 0.5, 1, 2, 3, 4, or 5 probes are present in each partition.

In some embodiments, the droplets that are generated are substantially uniform in shape and/or size. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the droplets that are generated are substantially uniform in volume. For example, the standard deviation of droplet volume can be less than about 1 picoliter, 5 picoliters, 10 picoliters, 100 picoliters, 1 nL, or less than about 10 nL. In some cases, the standard deviation of droplet volume can be less than about 10-25% of the average droplet volume. In some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

V. Amplification

DNA can be amplified following one or more rounds of reverse transcription. In some cases, the DNA can be amplified after first strand synthesis. In other cases, the DNA can be amplified following second strand synthesis. Methods for DNA amplification are well known in the art and include PCR, the ligase chain reaction (LCR), the transcription based amplification system (TAS), nucleic acid sequence-based amplification (NASBA), strand displacement amplification (SDA), rolling circle amplification (RCA), and hyper-branched RCA (HRCA).

Amplification can utilize one or more primers. In some cases, one or more of the amplification primers is the same as the first or second strand synthesis primer. For example, a gene specific first strand synthesis primer can be used as a first amplification primer in conjunction with a second amplification primer. In other cases, amplification primers are distinct from first and second strand DNA synthesis primers.

In some embodiments, amplification is performed in a complex mixture rather than in a set of partition mixtures. For example, multiple rounds of reverse transcription can be performed in a set of partition mixtures, the partitions can then be combined and then amplified. In some cases, the use of a barcode sequence or label on the first or second strand synthesis primer can allow one practicing the invention to determine which partition mixture an amplification reaction product derived from. Thus, although partitions are not necessarily kept physically intact, they are maintained.

In other embodiments, the amplification is performed in the same partition mixtures in which the reverse transcription is performed. Amplification reagents can be added to the partition mixtures by droplet fusion, micro channel flow, diffusion, or a combination thereof. In yet other embodiments, reverse transcription can be performed in a set of partition mixtures, the products can be recovered, and then amplification performed in a second set of partition mixtures.

VI. Digital Analysis

A digital readout assay, e.g., digital analysis, can be used to count the number of target molecules by partitioning the target molecules in a sample and identifying the partitions containing the target. Generally, the process of digital analysis involves determining for one or more partitions of a sample whether the partition is positive or negative for the presence of the target molecule or target molecules to be detected. For quantifying the amount of target molecule in a sample (e.g., quantifying the concentration or number of copies of a target molecule in a sample), the partitions are examined for the presence of an amplified target nucleic acid in each partition. A partition is "positive" for the presence of the target molecule if an amplified target nucleic acid is detected in the partition. In some embodiments, the amplified target nucleic acid is detected by detecting the presence of a signal generated by a label linked to a probe (e.g., a fluorescent, chemiluminescent, radioactive, or enzymatic label linked to a probe, such as an oligonucleotide, protein, peptide, or an aptamer probe). In some embodiments, the two or more probes are detected in the partition by detecting the production of a signal that is generated when two labeled probes are present in the same partition but not in the absence of one or both probes from the same partition. A partition is "negative" for the presence of the target molecule if no amplified target nucleic acid is detected.

In some embodiments, the method of detection comprises fluorescence detection. Methods of detecting accumulated amplification product using fluorescence are well known in the art. Examples of suitable approaches include, for example the use of use of intercalating dye, the use of labeled probes in conjunction with 5' nuclease cleavage, and the use of structured probes.

The use of intercalating dyes utilizes fluorogenic compounds that only bind to double stranded DNA. In this type of approach, amplification product (which in some cases is double stranded) binds dye molecules in solution to form a complex. With the appropriate dyes, it is possible to distinguish between dye molecules remaining free in solution and dye molecules bound to amplification product. For example, certain dyes fluoresce efficiently only when bound to double stranded DNA, such as amplification product. Examples of such dyes include, but are not limited to, SYBR Green and Pico Green (from Molecular Probes, Inc., Eugene, Oreg.), ethidium bromide, propidium iodide, chromomycin, acridine orange, Hoechst 33258, TOTO-I, YOYO-1, and DAPI (4',6-diamidino-2-phenylindole hydrochloride). Additional discussion regarding the use of intercalation dyes is provided, e.g., by Zhu et al., Anal. Chem. 66:1941-1948 (1994).

Fluorogenic nuclease assays are another example of a product quantification method that can be used successfully with the devices and methods described herein. The basis for this method of monitoring the formation of amplification product is to measure PCR product accumulation using a dual-labeled fluorogenic oligonucleotide probe, an approach frequently referred to in the literature as the "TaqMan" method.

The probe used in such assays can be a short (e.g., approximately 20-25 bases in length) polynucleotide that is labeled with two different fluorescent dyes. In some cases, the 5' terminus of the probe can be attached to a reporter dye and the 3' terminus attached to a quenching moiety. In other cases, the dyes can be attached at other locations on the probe. The probe can be designed to have at least substantial sequence complementarity with the probe-binding site on the target nucleic acid. Upstream and downstream PCR primers that bind to regions that flank the probe binding site can also be included in the reaction mixture. When the fluorogenic probe is intact, energy transfer between the fluorophore and quencher moiety occurs and quenches emission from the fluorophore. During the extension phase of PCR, the probe is cleaved, e.g., by the 5' nuclease activity of a nucleic acid polymerase such as Taq polymerase, or by a separately provided nuclease activity that cleaves bound probe, thereby separating the fluorophore and quencher moieties. This results in an increase of reporter emission intensity that can be measured by an appropriate detector. Additional details regarding fluorogenic methods for detecting PCR products are described, for example, in U.S. Pat. No. 5,210,015 to Gelfand, U.S. Pat. No. 5,538,848 to Livak, et al, and U.S. Pat. No. 5,863,736 to Haaland, each of which is incorporated by reference in its entirety, as well as Heid, C. A., et al., Genome Research, 6:986-994 (1996); Gibson, U. E. M, et al., Genome Research 6:995-1001 (1996); Holland, P. M., et al, Proc. Natl. Acad. Sci. USA 4 88:7276-7280, (1991); and Livak, K. J., et al., PCR Methods and Applications 357-362 (1995).

Structured probes (e.g., "molecular beacons") provide another method of detecting accumulated amplification product. With molecular beacons, a change in conformation of the probe as it hybridizes to a complementary region of the amplified product results in the formation of a detectable signal. In addition to the target-specific portion, the probe includes additional sections, generally one section at the 5' end and another section at the 3' end, that are complementary to each other. One end section is typically attached to a reporter dye and the other end section is usually attached to a quencher dye. In solution, the two end sections can hybridize with each other to form a stem loop structure. In this conformation, the reporter dye and quencher are in sufficiently close proximity that fluorescence from the reporter dye is effectively quenched by the quencher. Hybridized probe, in contrast, results in a linearized conformation in which the extent of quenching is decreased. Thus, by monitoring emission changes for the reporter dye, it is possible to indirectly monitor the formation of amplification product. Probes of this type and methods of their use is described further, for example, by Piatek, A. S., et al., Nat. Biotechnol. 16:359-63 (1998); Tyagi, S. and Kramer, F. R., Nature Biotechnology 14:303-308 (1996); and Tyagi, S. et al., Nat. Biotechnol. 16:49-53 (1998).

In some embodiments, a detector that is capable of detecting a signal or multiple signals is used to analyze each partition for the presence or absence of the target molecule. For example, in some embodiments a one or two-color reader (fluorescence detector) is used. The fraction of positive-counted partitions can enable the determination of absolute concentrations for the target molecule to be measured.

Once a binary "yes-no" result has been determined for each of the partitions of the sample, the data for the partitions is analyzed using an algorithm based on Poisson statistics to quantify the amount of target molecule in the sample. Statistical methods for quantifying the concentration or amount of a target molecule or target molecules is described, for example, in WO 2010/036352, which is incorporated by reference herein in its entirety.

VII. Kits

Kits containing compositions, and optionally, instructions for carrying out methods of the present invention are provided. For example, a kit can contain primers and/or enzymes and instructions for partitioning and carrying out multiple rounds of reverse transcription. Alternatively, the kit can contain one or more of enzymes, buffers, salts, nucleotides, reagents for forming partition mixtures, and detection reagents. The kit can further comprise instructions for partitioning and carrying out multiple rounds of reverse transcription.

What is claimed is:

1. A method of quantifying one or more target RNA(s) in a biological sample, the method comprising,
incubating a plurality of mixture partitions of the sample, wherein the mixture partitions are droplets, and wherein the mixture comprises the sample and a heat tolerant reverse transcriptase, under conditions such that at least two and up to 20 rounds of reverse transcription occurs in the partitions, wherein the rounds of reverse transcription are each terminated by a denaturation event, and wherein the denaturation event comprises heating the partition mixtures to a temperature above 55° C., thereby generating one or more cDNA(s) complementary to at least 10 contiguous nucleotides of the target RNA in partitions having the target RNA;
quantifying the number of partitions containing the cDNA(s); and
correlating the number of partitions containing the cDNA(s) to the quantity of the one or more target RNA(s) in the sample, thereby quantifying the one or more target RNA(s) in the sample.

2. The method of claim 1, wherein the incubating comprises incubating at least 100 mixture partitions.

3. The method of claim 1, comprising:
contacting the heat tolerant reverse transcriptase to the sample to form the mixture; and
partitioning the mixture to generate the plurality of partitions.

4. The method of claim 3, comprising performing the step of contacting the heat tolerant reverse transcriptase to the sample at a temperature of less than about 25° C.

5. The method of claim 3, wherein the heat tolerant reverse transcriptase comprises a hot start reverse transcriptase.

6. The method of claim 1, comprising:
partitioning the sample to generate the plurality of partitions; and
contacting the partitions with the heat tolerant reverse transcriptase, thereby generating the plurality of mixture partitions.

7. The method of claim 1, wherein the incubating comprises generating cDNA(s) comprising molecular barcodes such that cDNA(s) from different partitions can be distinguished; the method further comprising,
disrupting and combining the partitions to form a solution comprising barcoded cDNA(s); and
quantifying the number of partitions containing cDNA(s) by detecting the barcodes and counting a number of unique detected barcodes, wherein the number of unique detected barcodes is correlated with the number of mixture partitions containing the target RNA.

8. The method of claim 7, wherein the method further comprises quantifying multiple target RNAs by counting the number of unique detected barcodes of each of the cDNA(s) complementary to each target RNA, wherein the number of unique detected barcodes of each of the cDNA(s) complementary to each target RNA is correlated with the number of mixture partitions containing each target RNA.

9. The method of claim 1, wherein the denaturation conditions reduce secondary structure(s) in the target RNA, if present.

10. The method of claim 1, wherein the heat tolerant reverse transcriptase is Tth polymerase, and the partition mixtures comprise manganese ions.

11. The method of claim 1, wherein the quantifying comprises amplifying the cDNA(s).

12. The method of claim 11, wherein the quantifying comprises determining a relative level of two or more target RNAs from the same sample.

13. The method of claim 11, wherein the quantifying comprises determining an absolute level of two or more target RNAs from the same sample.

14. The method of claim 1, wherein the droplets are surrounded by an immiscible carrier fluid.

15. The method of claim 1, wherein the target RNA is present in the sample at a frequency of about 100 target RNA molecules per microliter or lower.

16. The method of claim 1, comprising 10-15 rounds of reverse transcription.

17. The method of claim 1, comprising 15-20 rounds of reverse transcription.

18. The method of claim 1, wherein the denaturation event comprises heating the partition mixtures to a temperature of at least 60° C.

* * * * *